United States Patent [19]

Nakamura et al.

[11] 4,266,028
[45] May 5, 1981

[54] PROCESS FOR PREPARATION OF PRODIGIOSIN

[75] Inventors: Katsumi Nakamura; Kumpei Kitamura, both of Takasaki, Japan

[73] Assignee: Kirin Beer Kabushiki Kaisha, Tokyo, Japan

[21] Appl. No.: 13,599

[22] Filed: Feb. 21, 1979

[51] Int. Cl.³ ............................................. C12P 17/16
[52] U.S. Cl. ..................................... 435/118; 435/881
[58] Field of Search ................. 195/96, 3, 30; 435/118

[56] References Cited

U.S. PATENT DOCUMENTS

| | | | |
|---|---|---|---|
| 2,658,024 | 11/1953 | Harned | 195/96 |
| 3,508,927 | 4/1970 | Herndon et al. | 195/96 |

OTHER PUBLICATIONS

Taplin et al., Am. J. Roentgenol. Radium Ther. Nucl. Med. 71, 294, 303, 304, (1954).
Kalesperis et al., J. Microbiol, 21 213, (1975).
Linnane et al., Aust. J. Sci. 16, 27 and 28, (1953).
Bunting, Cold Spring Harbor Symposia Quant. Biol. 11, 25–32, (1946).
Bunting, J. Bacterial, 40, 57 and 67, (1940).
Williams et al., J. Bacterial, 106, 438, (1971).
Bondarenko, Antibiotiki 9 814–819, (1965).
Methods in Enzymology, vol. XLIII, pp. 12 and 13, (1975).

*Primary Examiner*—Alvin E. Tanenholtz
*Attorney, Agent, or Firm*—Ladas & Parry

[57] ABSTRACT

Prodigiosin, an antibiotic, is effectively produced by culturing a novel *Serratia marcescens* R-2 strain. A synthetic culture medium is also provided, which contains a higher fatty acid having 12 to 18 carbon atoms, a salt thereof or an ester thereof as the sole or main source of carbon and in which a strain of *Serratia marcescens* having the abilities to assimilate the source of carbon and to produce prodigiosin can be cultivated to obtain prodigiosin.

4 Claims, No Drawings

PROCESS FOR PREPARATION OF PRODIGIOSIN

BACKGROUND OF THE INVENTION

1. Field of the Invention

This invention relates to microbiological processes for preparation of prodigiosin. More particularly, this invention relates to a process for preparation of prodigiosin by using a novel bacterial strain and a process therefor using a novel synthetic culture medium.

2. Description of the Prior Art

Prodigiosin is an antibiotic having antimicrobial activity against bacteria, fungi, protozoa and the like. Its clinical experiment on coccidioidomycosis has been reported [R. H. Wier et al., Am. J. Med. Sci. 224, 70 (1952)]. As to its toxicity, it has been reported that thrombosis was observed only at the site when a colloidal preparation comprising crystalline prodigiosin sample, ascorbic acid and glucose was intravenously administered [G. V. Taplin et al.: Am. J. Roentgenol. Radium Ther. Nucl. Med. 71, 294(1954)]. According to recent researches, prodigiosin has been reported to be a useful antibiotic which has little toxic effects on embryos [G. S. Kalesperis et al., Can. J. Microbiol. 21, 213 (1974)]. It is also known that prodigiosin has antitumor activity.

Prodigiosin has been produced by microbiological methods wherein the strains used include *Chromobacterium prodigiosum* (*Serratia marcescens*) ["Merck Index" 8th ed. (1968)] and *B. prodigiosus* (*Serratia marcescens*) ["Integrated English-Japanese Medical Dictionary," Nanzando (1971)]. These known strains, however, do not always exhibit a capability of producing prodigiosin in high yields. Thus, a strain having a capability of producing prodigiosin in high yields has been desired in the art.

On the other hand, a variety of culture media have been proposed for the microbiological processes. Solid media containing agar was employed, but the cultivation on a large scale was difficult. Liquid media took the place of the solid media. Among these media was a glycerol-peptone medium that produced prodigiosin most efficiently [M. I. Bunting: Cold Spring Harbor Symposia Quant. Biol. 11, 25 (1946)]. Problems reside in that it is a natural medium and requires expensive materials for the medium. However, all the other culture media including synthetic media did not provide as high industrial productivity of prodigiosin as the glycerol-peptone medium.

It has also been reported that the yield of prodigiosin was promoted when a certain higher unsaturated fatty acid such as oleic acid was incorporated into a certain medium [A. W. Linnane et al.: Australian J. Sci. 16, 27 (1953)].

SUMMARY OF THE INVENTION

The main object of this invention is to solve the above-mentioned problems hitherto accompanying the microbiological production of prodigiosin. This object and other objects have been achieved according to the present invention by using a novel *Serratia marcescens* strain as well as using a novel medium for the cultivation of *Serratia marcescens* strains.

A process for the preparation of prodigiosin according to one aspect of the present invention is characterized by the cultivation in a culture medium of the *Serratia marcescens* R-2 strain (as defined herein) to produce and accumulate prodigiosin in the bacterial bodies or the culture medium, and the separation and collection of the accumulated prodigiosin.

There is also provided a process for the preparation of prodigiosin according to another aspect of the present invention which is characterized by the cultivation, in a synthetic culture medium containing a higher fatty acid having 12 to 18 carbon atoms, a salt thereof and/or an ester thereof with an alcohol as the sole or main assimilable source of carbon, of a strain having the ability to assimilate the above-mentioned source of carbon and to produce prodigiosin, said strain being of *Serratia marcescens*, thereby to produce prodigiosin in the bacterial cells or the culture medium, and the separation of the produced prodigiosin.

The novel *Serratia marcescens* R-2 strain according to the present invention possesses a capability of producing prodigiosin in higher yields than the other strains tested, especially when the culture medium according to the present invention is used. The medium according to the present invention exhibits a capability to produce prodigiosin better than a conventional glycerol-peptone medium which has been the most effective of the known culture media for preparation of prodigiosin.

As mentioned above, it is known that a certain medium incorporated with a certain higher unsaturated fatty acid may promote production of prodigiosin to some extent. It has not been known, however, whether or not prodigiosin could be produced on a completely synthetic medium containing a higher fatty acid as the sole source of carbon. Moreover, it may be unexpected that prodigiosin can be produced on such a completely synthetic medium and, moreover, in a higher yield. In this respect, it should be noted that prodigiosin is not produced when a lower fatty acid is employed as the sole source of carbon.

The medium according to the present invention is simple in its composition and, therefore, the prodigiosin produced and accumulated can be readily separated and purified.

DETAILED DESCRIPTION OF THE INVENTION

1. R-2 Strain

The novel bacterial strain used in the present invention has the following bacteriological properties and was identified as belonging to *Serratia marcescens* in accordance with Bergey's "Manual of Determinative Bacteriology", 8th Ed.

(1) Bacteriological Properties

Source of isolation: Soil obtained at Takasakishi, Japan.

Morphological properties:

| (1) | Type | bacillus |
|---|---|---|
| (2) | Dimension | 0.2 to 0.6 × 1.0 to 1.8μ |
| (3) | Motility | with limbic flagella, motile |
| (4) | Gram stain | negative |

Cultural properties:

Good growth on a bouillon-agar plate culture or slant culture. Smooth surface and clear periphery. Red color. Viscous.

Physiological properties:

| (1) | Growth temperature | 15 to 34° C. |

-continued

| | | |
|---|---|---|
| (2) | Growth pH | pH 5 to 10, most preferably pH 7.5 |
| (3) | Oxygen-demand property | facultative aerobic |
| (4) | Catalase production | positive |
| (5) | Nitrate reduction | positive |
| (6) | Methylene-blue reduction | positive |
| (7) | Gelatin emulsification | layered emulsification |
| (8) | Action on B.C.P. milk | coagulation and peptonization due to protease |
| (9) | Indole production | indefinite |
| (10) | Hydrogen sulfide production | positive |
| (11) | Ammonia production | positive |
| (12) | Acetylmethyl-carbinol production | positive |
| (13) | Methyl-red test - Acid formation | negative |
| (14) | Diastase production | negative |
| (15) | Decomposition of carbohydrates (Hugh and Leifson's culture media) | |
| | (a) Glucose, fructose, maltose, sucrose, glycerol | Produced acids aerobically and anaerobically, generated no gas. |
| | (b) Xylose | Produced acids slowly in aerobic condition and very slowly in anaerobic condition, generated no gas. |
| | (c) Lactose | Produced acids very slowly, generated no gas. |
| | (d) Arabinose | Produced acids very slowly in aerobic condition only, generated no gas. |
| | (e) Starch | Produced no acid, generated no gas. |
| (16) | Nitrate respiratory ability | positive, but denitrification is negative |
| (17) | DNase Test | positive |
| (18) | Nucleoside phosphotransferase test | produced 5'-nucleotide. |

(2) Deposition of the Strain

The *Serratia marcescens* R-2 strain used in the present invention was deposited on Mar. 26, 1977 with Fermentation Research Institute, Agency of Industrial Science and Technology, Inage, Chiba City, Japan, under FERM P No. 3995, and was deposited on Nov. 10, 1978 with American Type Culture Collection, 12301 Parklawn Drive, Rockville, Md. U.S., under ATCC No. 31453.

2. Other Strains

The *Serratia marcescens* strains which can be grown in the present synthetic culture medium and have the ability to produce prodigiosin include, in addition to the R-2 strain, IAM 1136, and IAM 1022.

3. Culture Medium

The synthetic medium according to the present invention which is to be generally used for prodigiosin-producing bacteria of *Serratia marcescens*, is specified from the standpoint of assimilable carbon sources.

(1) Source of carbon

The synthetic medium according to the present invention is characterized by its assimilable carbon source, wherein a higher fatty acid having 12 to 18 carbon atoms, a salt thereof, an ester thereof or mixtures of these compounds are used as the sole or main assimilable source of carbon.

For the higher fatty acid, a saturated or unsaturated monocarboxylic acid is especially preferred, and oleic acid is most suitable.

The salts of the higher fatty acid include alkali metal salts, alkali earth metal salts, manganese salts, iron salts, ammonium salts and the like. The water-soluble salts thereof are preferred. These salts are generally represented by the alkali metal salts or ammonium salt of oleic acid.

The esters of the higher fatty acid include such as lower alkyl esters, preferably $C_1$ to $C_4$ alkyl esters, e.g. methyl esters, ethyl esters, n-butyl esters, polyoxyethylene-sorbitan esters (Tween, trade-name) and the like. These esters are generally represented by the $C_1$ to $C_4$ alkyl esters of oleic acid.

These higher fatty acid compounds can be used in a reasonable concentration provided that the compounds of a given concentration do not inhibit the growth of the bacteria. A suitable concentration is generally in the range of 0.5 to 10% and preferably in the range of 1 to 3.5% by weight.

(2) Other sources of nutrient

The culture medium according to the present invention is characterized by containing the above-mentioned higher fatty acid compounds as the sole or main assimilable source of carbon, but can further contain other assimilable sources of nutrient or auxiliary components which are required or desired.

As an assimilable source of nitrogen, a variety of inorganic and organic nitrogen compounds which have been generally employed in conventional media can be used. When the ammonium salts of the higher fatty acid are employed, the salt can serve as the sources of both carbon and nitrogen. Ammonium sulfate is most preferred as the source of nitrogen. The effect of ammonium sulfate is considered to be partly due to the presence of sulfate ions. Thus, production of prodigiosin can be enhanced by the addition of sulfate ions to the culture medium when a source of nitrogen other than ammonium sulfate is used. The source of nitrogen is used in a concentration normally equipped in conventional media and preferably in the range of 0.1 to 1%.

Other components which have been employed in conventional synthetic media such as phosphates and magnesium salts are essential or advantageous for use in the present invention. These salts can be used in concentrations normally employed in conventional synthetic media.

In order to promote the production of prodigiosin, manganese ions or ferrous or ferric ions can be added to the culture medium according to the present invention. A suitable surface active agent can be added to the medium to release the resulting prodigiosin therefrom. When the above-mentioned higher fatty acid compound is water-insoluble, the surfactant is also useful for emulsifying the compound. The surfactant preferably used in the present invention is represented by the salts of higher fatty acids such as the higher fatty acid used as the assimilable carbon source, and "Triton X-100".

The starting pH of the culture medium is generally in the range of 6.5 to 9.5 and preferably in the range of 7.0 to 9.0. The medium is adjusted to a pH within these ranges with a suitable acid or alkali such as hydrochloric acid or sodium hydroxide.

The culture medium according to the present invention is typically a completely synthetic medium, but a natural-medium component can be concomitantly used therein if so desired.

(3) Other culture media

The novel R-2 strain is preferably cultivated in the above-mentioned synthetic medium. For cultivation of the R-2 strain, however, it is not essential that the medium be the synthetic medium containing the above-mentioned fatty acid compound as the sole assimilable source of carbon, and other media containing an assimilable carbon source in place of or in addition to the fatty acid compound can also be utilized. An example of such media is a glycerol-peptone medium.

4. Conditions on Cultivation

Cultivation of the strains can be carried out in solid and liquid media. An aerobic cultivation in liquid media is most preferred to produce and obtain prodigiosin in large quantities.

The temperature of cultivation is generally in the range of about 16° to 34° C. and most preferably in the vicinity of about 28° C. The cultivation is conducted with aeration and stirring and is generally terminated in 2 or 3 days.

5. Recovery of Prodigiosin

Recovery of prodigiosin from a liquid medium is carried out by combining conventional procedures for separation of natural organic compounds. Of course, known methods which have been employed for separation and purification of prodigiosin can be utilized. For example, a preferable process for separation and purification comprises extracting prodigiosin with a solvent, saponifying the basic prodigiosin with sulfuric acid, hydrochloric acid or perchloric acid to prepare the corresponding salt, and then converting the salt back to free-state prodigiosin, followed by recrystallization with hot ethanol-ammonia water and the like.

In an actual instance of practice the prodigiosin thus purified was in the form of red crystals, and its analytical data were in fair agreement with the corresponding values found in literature with respect to elemental analysis, visible and ultraviolet absorption spectra, infrared absorption spectra and mass spectra, some of which are shown below.

(1) Elemental analysis

|  | N | C | H | O |
|---|---|---|---|---|
| Found | 12.26 | 74.97 | 7.98 | 4.79 |
| Calculated* | 12.99 | 74.27 | 7.79 | 4.79 |

*Molecular formula. $C_{20}H_{25}N_3O$ (2) Visible and Ultraviolet Spectra

| 0.1 N HCl-methanol | |
|---|---|
| $\lambda_{max}$ | = 534 m$\mu$ |
| 0.1 N NaOH-methanol | |
| $\lambda_{max}$ | = 467 m$\mu$ |
| isopropanol | |
| $\lambda_{max}$ | = 466 m$\mu$, 336 m$\mu$, 280 m$\mu$ |

Non-limitative examples are given hereinbelow.

EXAMPLE 1

Comparison of the yield of prodigiosin produced in the present fatty acid medium with those in the conventional media was made as follows.

Experimental method

One standard platinum loop amount of *Serratia marcescens* R-2 strain which had been preserved on a bouillon slant medium was inoculated on a bouillon liquid medium 100 ml. and incubated at 30° C. for 24 hours by means of a shake culture, to obtain a preliminary culture solution. To 50 ml. each of the culture media shown in Table 1, 0.5 ml. each of the culture solution was inoculated and incubated at 30° C. for 2 days by means of a shake culture method. Measurement of prodigiosin was carried out by extracting 1 ml. of the resulting culture solution with 9 ml. of an acidic methanol (4 parts by volume of 1 N HCl+96 parts by volume of methanol) and subjecting the extract to centrifuging to obtain a supernatant liquid, followed by colorimetric determination at 534 m$\mu$ of the supernatant.

Results

The results thus obtained are shown in Table 1.

TABLE 1

| No. | Media | Yield (mg/lit.) of prodigiosin | Compositions of Media |
|---|---|---|---|
| 1 | medium according to the present invention | 144.9 | sodium oleate 2%, $(NH_4)_2SO_4$ 0.4%, $KH_2PO_4$ 0.3%, $MgSO_4$ 0.05%, tap water pH 8 |
| 2 | medium according to Harned[1] | 12.9 | mannite 1%, meat extract 0.5%, $MgSO_4$ 0.1%, pure water pH 7.2 |
| 3 | PG medium according to Bunting[2] | 97.6 | glycerol 1%, peptone 0.5%, pure water pH 7.2 |
| 4 | minimum medium according to Bunting[3] | 2.1 | glycerol 1%, ammonium citrate 0.5%, $K_2HPO_4$ 1%, $MgSO_4$ 0.05%, NaCl 0.05%, ferrous ammonium citrate 0.005%, pure water pH 7.2 |
| 5 | complete medium according to Williams[4] | 5.5 | medium 4 mentioned above + yeast extract 0.1% + bactocasiton 0.2%, pure water pH 7.2 |
| 6 | medium according to Bondarenko[5] | 0 | $K_2HPO_4$ 0.1%, $KH_2PO_4$ 0.25%, $NaNO_3$ 0.25%, $(NH_4)_2SO_4$ 0.1%, NaCl 0.05%, glucose 0.5%, pure water pH 7.2 |
| 7 | bouillon medium | 2.3 | bouillon powder 2% |

Note:
[1] Harned, R.L.: U.S. 2658024, Nov. 3 (1953)
[2] Bunting, M.I.: Cold Spring Harbor Symposia Quant. Biol., 11, 25 (1946)
[3] Bunting, M.I.: J. Bacteriol., 40, 57 (1940)
[4] Williams, R.P.: J. Bacteriol., 106, 438 (1971)
[5] Bondarenko, B.N.: Antibiotiki., 9, 814 (1965)

As clearly shown in Table 1, a marked quantity of prodigiosin was produced in the sodium oleate medium, which was far superior to the other completely-synthetic media and was also better than the natural peptoneglycerol medium according to Bunting.

EXAMPLE 2

In order to evaluate the effects of various fatty acids and esters thereof used as the source of carbon, these substances were substituted for sodium oleate in the completely synthetic medium, shown in Table 1, comprising sodium oleate 2%, ammonium sulfate 0.4%, monopotassium phosphate 0.3%, and magnesium sulfate 0.05% (pH 8.0). The preliminary cultivation, regular cultivation and measurement were carried out in the same way as those for obtaining the data in Table 1. Propagation was measured by diluting 10-fold the resulting culture solution with mixed organic solvents (butanol, ethanol and chloroform; 10:10:1) and effecting turbidometric determination at 660 m$\mu$ of the resulting mixture.

The results are shown in Table 2.

TABLE 2

| Source of carbon | Yield (mg/lit.) of prodigiosin | Propagation ($A_{660}$) |
|---|---|---|
| Acetic acid ($C_2$) | 0 | 0 |
| Butyric acid ($C_4$) | 0 | 0 |
| Caproic acid ($C_6$) | 0 | 0 |
| Caprylic acid ($C_8$) | 0 | 0 |
| Capric acid ($C_{10}$) | 0 | 0 |
| Lauric acid ($C_{12}$) | 9.0 | 0.069 |
| Myristic acid ($C_{14}$) | 3.2 | 0.146 |
| Palmitic acid ($C_{16}$) | 5.5 | 0.131 |
| Stearic acid ($C_{18}$) | 0.4 | 0.055 |
| Oleic acid ($C_{18} = 1$) | 144.9 | 0.430 |
| Linoleic acid ($C_{18} = 2$) | 5.0 | 0.196 |
| Linolenic acid ($C_{18} = 3$) | 8.9 | 0.171 |
| Triolein | 0 | 0.698 |
| Tween 80 | 10.5 | 0.172 |
| Methyl oleate | 17.9 | 0.195 |
| Ethyl oleate | 171.1 | 0.221 |
| n-butyl oleate | 6.1 | 0.083 |

As shown in Table 2, the *Serratia marcescens* R-2 could hardly assimilate lower fatty acids having $C_2$–$C_{10}$ atoms, but could well assimilate higher fatty acids having $C_{12}$–$C_{18}$ atoms to produce prodigiosin. Oleic acid among higher fatty acids was somewhat specific in the yield of prodigiosin. Esters of oleic acid such as Tween 80 and Tween 85 were also assimilated to produce prodigiosin. Triolein was well assimilated, but no prodigiosin was produced.

EXAMPLE 3

Several *Serratia marcescens* strains, of which the sources were known, were cultivated in oleic acid media to produce prodigiosin in order to confirm whether or not the property to produce prodigiosin from higher fatty acids and especially oleic acid is peculiar to the *Serratia marcescens* R-2 strain. The preliminary cultivation, regular cultivation and measurement were carried out in the same way as in Example 2.

Similar experiments were also carried out in order to determine whether or not the novel R-2 strain can be cultured in some media other than the medium according to the present invention.

The results are shown in Table 3. Incidentally, all the strains used in this example belong to *Serratia marcescens*.

TABLE 3

| | Media | | | |
|---|---|---|---|---|
| | This invention | | | |
| Strain | Yield (mg/lit.) of prodigiosin | Propagation ($A_{660}$) | PG[1] Yield (mg/lit.) of prodigiosin | Harned[2] Yield (mg/lit.) of prodigiosin |
| R-2 | 144.9 | 0.430 | 97.6 | 12.9 |
| IAM 1136 | 55.3 | 0.471 | 67.9 | 12.6 |
| IAM 1022 | 68.5 | 0.470 | — | — |
| IAM 1105 | 1.8 | 0.445 | 70.3 | 2.2 |
| IAM 1061 | — | — | 97.7 | 0 |
| IAM 1104 | — | — | 3.7 | 0 |
| IAM 1162 | 0 | 0.091 | 2.9 | 0 |
| IAM 1065 | 0 | 0.571 | 0 | 0 |
| IAM 1021 | 0 | 0.447 | 0 | 0 |

Note:
[1] No. 3 in Table 1
[2] No. 2 in Table 1

As shown in Table 3, most of the strains of *Serratia marcescens* can assimilate oleic acid, which can be classified into a group that can produce prodigiosin and a group that cannot. This may be interesting from the view-point of taxology.

The R-2 strain according to the present invention can be cultivated in some media other than the medium according to the present invention, but in such a case, it was found that the R-2 strain is not as superior to other strains as it is when cultivated in the culture medium of the present invention.

EXAMPLE 4

The *Serratia marcescens* R-2 strain was inoculated on a 2 liter oleic acid medium and subjected to a shake culture at 30° C. for 48 hours. The resulting culture liquid was inoculated on a 100 liter oleic acid medium and incubated in a jar fermentor at 30° C. for 3 days with aeration and stirring. The resulting culture liquid was saturated with 40% ammonium sulfate and allowed to stand overnight at 8° C. The floating bacterial cells were then filtered with a diatomaceous earth, and the collected bacterial cells were subjected to freeze-drying to obtain about 3 kgs. of the freeze-dried bacterial cells including the diatomaceous earth.

Then, 1.5 kgs. of the freeze-dried bacterial cells were extracted with 8 liters of ethanol, and to the resulting filtrate was added 5 liters of water, and 3N NaOH was further added dropwise thereto until the solution turned to yellow color. From the alkaline solution, the colored substance was extracted with 8 liters of hexane, washed with water, stirred with 3 liters of 1 N $H_2SO_4$, and allowed to stand overnight at 4° C. The resulting sulfate was filtered, and collected sulfate was dissolved in 200 ml. of ethanol. Then the same volume of water was added to the resulting solution, and thereafter 3 N NaOH was added thereto in a large excess quantity after the solution turned to yellow color. This was followed by extraction with 500 ml. of hexane.

The resulting hexane layer was washed with water, dehydrated, and concentrated under reduced pressure. The residue was recrystallized from a hot ethanol-ammonia water to obtain primary free crystals. The crystals were dissolved in petroleum ether, stirrred with MgO, and filtered. The filtrate was concentrated under reduced pressure. The resulting residue was recrystallized from a hot ethanol-ammonia water to obtain 380 mgs. of secondary free crystals. The mother liquor of the primary free crystals was treated in the same way to recover another 190 mgs. of secondary crystals.

Prodigiosin, as mentioned above, has been reported to have a variety of physiological activities. Some physiological activities were studied with respect to the crystalline prodigiosin prepared in the Examples of the present invention. As a result, it was found to exhibit marked antimicrobial activities against Gram-positive bacteria, actinomyces and fungi.

What is claimed is:

1. A process for preparation of prodigiosin, which comprises cultivating *Serratia marcescens* R-2 strain having an ATCC number of 31453 in a culture medium, thereby to produce prodigiosin in the bacterial cells or the medium, and collecting the produced prodigiosin.

2. A process for preparation of prodigiosin, which comprises cultivating, in a synthetic culture medium containing 0.5 to 10% by weight of a polyoxyethylene-sorbitan ester of a higher fatty acid having 12 to 18 carbon atoms as the sole or main assimilable source of carbon, a bacterial strain having the capability of assimilating the source of carbon and producing prodigiosin, said strain being a *Serratia marcescens* strain, thereby to produce prodigiosin in the bacterial cells or the medium; and separating the produced prodigiosin.

3. A process for preparation of prodigiosin, which comprises cultivating, in a synthetic culture medium containing 0.5 to 10% by weight of a higher fatty acid having 12 to 18 carbon atoms, a salt thereof and/or $C_1$ to $C_4$ alkyl ester thereof with an alcohol as the sole or main assimilable source of carbon, a bacterial strain having the capability of assimilating the source of carbon and producing prodigiosin, said strain being a *Serratia marcescens* strain having an ATCC number of 31453, thereby to produce prodigiosin in the bacterial cells or the medium; and separating the produced prodigiosin.

4. The process as set forth in claim 3, in which the source of carbon is selected from the group consisting of oleic acid, alkali metal salts of oleic acid, ammonium salt of oleic acid and $C_1$ to $C_4$ alkyl esters of oleic acid.

* * * * *